United States Patent
Esposito

(12) 
(10) Patent No.: US 6,214,290 B1
(45) Date of Patent: Apr. 10, 2001

(54) NON-CYTOTOXIC POLYURETHANE MEDICAL ITEMS

(75) Inventor: Guy Esposito, Beynost (FR)

(73) Assignee: Hospal Industrie, Meyzieu (FR)

( * ) Notice: Subject to any disclaimer, the term of this patent is extended or adjusted under 35 U.S.C. 154(b) by 0 days.

(21) Appl. No.: 09/127,596

(22) Filed: Jul. 31, 1998

(30) Foreign Application Priority Data

Jul. 31, 1997 (FR) .................................................. 97 10036

(51) Int. Cl.⁷ ....................................................... A61L 2/00
(52) U.S. Cl. .................... 422/1; 210/321.61; 210/321.71; 422/22; 422/28; 422/44; 422/45; 428/423.1; 528/48
(58) Field of Search .............................. 422/28, 1, 44–45, 422/22; 528/48; 210/321.61, 321.71; 428/423.1

(56) References Cited

U.S. PATENT DOCUMENTS 3,920,588 * 11/1975 Traubel et al. .
4,123,412   10/1978 Fukuda et al. .
4,879,032 * 11/1989 Zemlin ............................ 210/321.61
5,932,352 * 11/1975 Higgins ............................ 428/423.1

FOREIGN PATENT DOCUMENTS 2 268 058   11/1975 (FR) .

* cited by examiner

Primary Examiner—Krisanne Thornton
(74) Attorney, Agent, or Firm—Millen, White, Zelano & Branigan, P.C.

(57) ABSTRACT

The invention relates to articles of manufacture of polyurethane-generating compositions for the manufacture of non-cytotoxic products for medical use, characterized in that these compositions contain: at least one polyisocyanate, preferably a non-aromatic polyisocyanate, in the monomer or prepolymer state; at least one polyol; and at least one dialkyl sulphoxide compound, preferably in the proportion of at least 2% by weight with respect to the total weight of the polyol or polyols.

19 Claims, No Drawings

NON-CYTOTOXIC POLYURETHANE MEDICAL ITEMS

FIELD OF THE INVENTION

The subject-matter of the invention is medical items based on polyurethane-generating compositions which are non-cytotoxic after sterilization or disinfection by an oxidizing process and more particularly potting bodies for flat-membrane or hollow-fiber medical exchangers. Another subject-matter of the invention is a process for the preparation of these polyurethane medical items which makes it possible to greatly limit the cytotoxicity resulting from the sterilization or from the disinfection by an oxidizing process, such as ionizing radiation (gamma radiation, electron beam), gaseous peroxides (so-called cold plasma sterilization), liquid peroxides or any other physical or chemical process involving an oxidation reaction capable of denaturing the sterilized material.

Depending on the situation, the polyurethane potting bodies are intended to form:

a cylindrical partition for separating the two compartments of a medical exchanger, the membrane of which is composed of a bundle of hollow fibers. The operation which consists in producing such a separating partition is usually denoted under the term "potting";

or a leaktight seal in a medical exchanger comprising a semi-permeable flat membrane. The operation which consists in producing such a seal is usually denoted under the term "leaktightness packing". Nevertheless, in order to simplify the present description, this operation will also be denoted under the term "potting".

Out of concern for clarity of the present description, the term "seal" will be used to denote without distinction a leaktight seal in semi-permeable flat-membrane medical exchangers or a cylindrical separating partition in medical exchangers in which the membrane is composed of a bundle of semi-permeable hollow fibers.

The present invention is in particular of use in the manufacture of exchangers for medical applications in the form, for example, of dialysers, haemofilters and oxygenators.

BACKGROUND OF THE INVENTION

It is common practice to manufacture exchangers for medical applications by following the general stages which follow:

preparing a semi-permeable membrane from a flat membrane or conforming a bundle of semi-permeable hollow fibers from hollow fibers;

mounting the semi-permeable membrane or else the bundle of hollow fibers in a casing and forming, depending on the situation, a leaktight seal or a cylindrical partition for separating the two compartments, using a polyurethane-generating adhesive composition;

if appropriate, attaching end fittings to the casing and sterilizing the medical device obtained.

The polyurethane-generating adhesive compositions used to prepare a seal in a medical exchanger generally comprise, before polymerization, one or more polyiso-cyanates, one or more polyols and, optionally, one or more polyfunctional crosslinking agents and/or one or more catalysts.

The polyurethane, once it is cured, has the essential function of forming a leaktight seal, in order for there to be no infiltration between the two compartments of the exchangers or with the outside. The risk of infiltration must in particular be avoided between the blood compartment and the dialysate compartment of medical exchangers for blood treatment. To achieve this, the polyurethane adhesive composition must exhibit satisfactory adhesion with the semi-permeable membranes of the exchangers, whatever the chemical nature of the materials of which they are composed. This composition must also exhibit satisfactory adhesion with the components of the exchangers with which it is brought into contact, such as the casing.

Another important quality required of exchangers for biomedical use is the biocompatibility of cured and sterilized polyurethane potting bodies, more especially their non-cytotoxicity. Otherwise, the stage of sterilization or of disinfection by an oxidizing process, in particular when it is a sterilization by irradiation, can render polyurethane cytotoxic.

Previously, in order to form non-cytotoxic potting bodies, various solutions were provided, thus:

in U.S. Pat. No. 4,332,927, provision was made for polyurethane-generating compositions comprising at least one prepolymer with isocyanato endings (—NCO), at least one polyol and a catalytic amount of a dicarboxylated dialkyltin compound;

in European Patents No. 0,393,545 and No. 0,413,265 and U.S. Pat. No. 5,306,798, various polyurethane-generating adhesive compositions based on diphenylmethane diisocyanates (MDI) or on MDI derivative, and on specific polyols, were provided.

SUMMARY OF THE INVENTION

It has now been found, differently and surprisingly, that it is possible to manufacture polyurethane medical articles sterilized or disinfected by an oxidizing process which are non-cytotoxic, in particular polyurethane potting bodies, which are, in addition, sufficiently adhesive to semi-permeable membranes of exchangers but non-cytotoxic after sterilization or disinfection by an oxidizing process. In accordance with the invention, the starting point is a polyurethane-generating composition comprising:

at least one polyisocyanate, preferably a non-aromatic polyisocyanate, in the monomer or prepolymer state;

at least one polyol in the monomer or prepolymer state; and at least one dialkyl sulphoxide compound, preferably in the proportion of at least 2% by weight of the total weight of the polyol or polyols.

(Dialkyl sulfoxide is mentioned in a completely different context as an anti-slag additive to urethane-base materials in U.S. Pat. No. 4,123,412.)

Advantageously, the polyurethane-generating composition additionally comprises at least one catalyst of the polymerization reaction of a polyisocyanate and of a polyol.

Another subject-matter of the present invention is a process which makes it possible to reduce the cytotoxicity of polyurethane medical items, in particular polyurethane potting bodies, liable to appear after sterilization or disinfection by an oxidizing process, characterized in that the polyurethane-generating composition is prepared from:

at least one polyisocyanate, preferably a non-aromatic polyisocyanate, in the monomer or prepolymer state;

at least one polyol;

at least one dialkyl sulphoxide compound, the amount of dialkyl sulphoxide compound preferably being at least equal to 2% by weight with respect to the total weight of the polyols; and if appropriate, at least one catalyst of the polymerization reaction of a polyisocyanate and of a polyol.

Still another aspect of the invention can be characterized as an improved article of manufacture comprising a potting compound in contact with a flat membrane or hollow fiber medical exchanger, wherein the improvement comprises the nature of the potting compound as described herein.

In the context of the present invention, the term non-cytotoxic polyurethane medical items is understood to mean items resulting in a percentage of inhibition of cell growth (% ICG) which is greatly reduced by virtue of the presence of at least one dialkyl sulphoxide compound. This percentage of ICG is preferably at most equal to 30% on average over at least 3 samples, when the polyurethane medical items are subjected to the biological tests of medical and dental equipment and devices, part 5: in vitro methods, of the ISO Standard 10-993, supplemented by the conditions for measurement of cytotoxicity used by the assignee company. These specific conditions for measurement of cytotoxicity are set out hereinbelow, with the examples.

An essential characteristic of the invention lies in the use of at least one dialkyl sulphoxide compound for preparing non-cytotoxic polyurethane medical items, more especially potting bodies intended for coating medical exchangers in the form of flat membranes or hollow fibers.

The alkyl radicals of the dialkyl sulphoxide compounds suitable for the invention can comprise one or more functional groups such as hydroxyl groups but are devoid of functional groups which react sharply with an isocyanato group, such as amine groups or thiol groups.

The dialkyl sulphoxide compounds suitable for the invention have a melting point at most equal to 40EC and must not be toxic to man in the event of diffusion into the blood. Dialkyl sulphoxide compounds which are liquid at ambient temperature, that is to say at a temperature of the order of 20–25EC, are advantageously chosen. The preferred dialkyl sulphoxide compound is dimethyl sulphoxide, better known under the abbreviation "DMSO".

Preferably, the amount of DMSO to be provided in order to achieve satisfactory results in the cytotoxicity test (i.e., preferably at most 30% inhibition of cell growth on average over at least 3 samples) is at least equal to 2% by weight of the total weight of the polyol or polyols. It is preferable for the amount of DMSO not to exceed 10% by weight (with respect to the total weight of the polyols), otherwise a plasticizing effect leading to a decrease in hardness may express itself in the polyurethane. It is also preferable for the amount of DMSO to be between 3% and 9% by weight with respect to the total weight of polyols.

Use may be made, as examples of polyols capable of being suitable for the invention, of: castor oil; esters of polyol and of ricinoleic acid; polyether polyols, such as polyoxypropylene glycol and polytetramethylene ether glycols; homopolymers or copolymers of butadiene carrying at least two hydroxyl groups; esters of polyol and of fatty acid, such as soybean oil or castor oil, or esters of saturated or unsaturated diacid and of ethylene glycol, such as the adipate of poly(ethylene glycol); N,N,N',N'-tetrakis (hydroxypropyl)-ethylenediamine; polycaprolactone polyols; polyol oligomers, in particular polyol dimers which can comprise a cyclic and saturated hydrocarbon group and which are formed by condensation and complete reduction of two unsaturated fatty acids, or formed by condensation, partial reduction and esterification of two unsaturated fatty acids; prepolymer polyols obtained by reaction of an excess of polyols with a polyisocyanate, preferably a non-aromatic polyisocyanate; mixtures of two or more of the abovementioned polyols.

The polyisocyanates which are suitable for the invention are preferably non-aromatic, that is to say devoid of one or more benzene, naphthalene or anthracene nuclei, and the like. Mention may be made, as examples of non-aromatic polyisocyanates, in the monomer or prepolymer state, capable of being suitable for the invention, of aliphatic or cycloaliphatic polyisocyanates, such as dicyclohexylmethyl 4,4'-diisocyanate (HMDI), isophorone diisocyanate (IPDI), corresponding to 3-isocyanatomethyl-3,5,5-trimethylcyclohexyl isocyanate, trimethylhexamethylene diisocyanate, hexamethylene diisocyanate (HDI) and its condensation derivatives, such as HDI biuret and HDI isocyanurate. Aromatic polyisocyanates can also be used.

The amount of polyisocyanate reacted with the polyol should be sufficient to provide at least one isocyanato group per polyol hydroxyl group. An NCO/OH ratio by number equal to or greater than 1, preferably equal to or greater than 1.1, is advantageous.

Of course, the polyurethane compositions according to the invention can comprise various additives conventionally used in the technical field involved, such as:

at least one catalyst for accelerating the crosslinking, preferably in the proportion of 0.01 to 2% by weight of the overall composition. Mention may be made, as example of catalyst suitable for the present invention, of tin carboxylates, such as dibutyltin dilaurate (DBTL). The presence of a catalyst is recommended when the polyisocyanates are non-aromatic;

at least one adhesion promoter for conferring, on the cured polyurethane, improved adhesion to the semi-permeable flat membranes or hollow fibers, in particular when the medical exchanger is composed of a negatively charged semi-permeable membrane [i.e. a membrane comprising negative charges in excess which can be detected, in particular by flow measurements (Zeta potential)]. As adhesion promoter, use may be made of the polyamine of formula (I) disclosed in European Patent Application No. 0,573,310 or of a polyethyleneimine (PEI). A PEI with a weight-average molecular mass ranging from approximately 600 to approximately 10,000, easier to process due to their lower viscosity at ambient temperature, is preferably chosen. The PEI can be processed according to two different processes (a) or (b) which follow:

a) the PEI can be used to treat the outer surface of the semi-permeable membranes. It is then applied to the outer surface of the fibers or of the channels formed by the flat semi-permeable membranes;

b) the PEI can be incorporated in the polyurethane-generating adhesive composition. It is then mixed with one or more of the components which are used to prepare a polyurethane-generating adhesive composition.

A patent representative of the technique of the use of PEI as adhesion promoter for potting bodies is European Patent Application No. 0,710,683.

Various processes can be used for the preparation of the polyurethane medical items according to the invention.

In accordance with a preferred embodiment, a polyurethane-generating composition is prepared from two components which are stored separately, respectively a first component composed of at least one polyisocyanate, in the monomer or prepolymer state, and a second component composed of at least one polyol and of at least one dialkyl sulphoxide compound, preferably in the proportion of at least 2% by weight of dialkyl sulphoxide compound with respect to the total weight of the polyol or polyols, and, if appropriate, of at least one catalyst and/or of at least one adhesion promoter. These two components are mixed, until a homogeneous mixture is obtained, at the time of the manufacture of the medical item, such as a leaktight polyurethane seal.

The polyurethane-generating composition can also be presented, before use, as three components, respectively a first component composed of at least one poly-isocyanate, in the monomer or prepolymer state, a second component composed of at least one polyol and, depending on the case, of at least one catalyst and/or at least one adhesion promoter, and a third component composed of at least one dialkyl sulphoxide compound, preferably in the proportion of at least 2% by weight with respect to the weight of the polyol or polyols.

The polyurethane-generating adhesive compositions according to the invention are particularly well suited to negatively charged semi-permeable membranes and are conformed into a single type of material which comprises in particular an acrylonitrile homo- or copolymer in the form of a flat membrane or of a bundle of hollow fibers.

Such a material, when it is composed of one or more acrylonitrile copolymers, can comprise:

(1) a copolymer of acrylonitrile and of at least one anionic or anionizable monomer comprising, if appropriate, units originating from at least one other monomer containing olefinic unsaturation capable of being copolymerized with the acrylonitrile, or (2) a copolymer of acrylonitrile and of at least one anionic or anionizable monomer and of at least one non-ionic and nonionizable monomer.

Some of these macromolecular compounds, and the various monomers capable of being used as starting materials in their manufacture, are more fully disclosed in U.S. Pat. No. 4,545,910, regranted under Re. No. 34239.

Among these macromolecular compounds, those with which the polyurethane-generating adhesive compositions according to the invention are particularly well suited are defined under (1) above, in particular when the semi-permeable membrane is in the hydrogel state. In particular, the invention is particularly well suited to those in which the anionic or anionizable comonomer is olefinically unsaturated and carries anionic groups chosen from sulphonate, carboxyl, phosphate, phosphonate and sulphate groups and more particularly still when this comonomer is sodium methallylsulphonate.

Of course, the precise nature of the counterion of the anionic groups is not essential to the satisfactory operation of the invention.

Mention may be made, among monomers containing olefinic unsaturation capable of being copolymerized with acrylonitrile, of alkyl acrylates and, in particular, methyl acrylate.

The examples below illustrate the invention without in any way limiting the scope thereof.

EXAMPLES 1 AND 2

Preparation of a Polyurethane (PUR) from an Adhesive Composition in Two Components, Incorporating or not Incorporating a Dialkyl Sulphoxide Compound.

A specific amount of polyol is introduced into a vessel equipped with a stirrer. A specific amount of adhesion promoter is weighed out and this amount is introduced into the vessel. If appropriate, a specific amount of dialkyl sulphoxide compound is weighed out and this amount is introduced in its turn into the vessel. Stirring is then carried out, under a nitrogen or dry air atmosphere, until the mixture is homogenized. The mixture is subsequently degassed under vacuum, at ambient temperature or under warm conditions (maximum 40EC), before it is used in the preparation of the polyurethane by mixing with isocyanate, itself degassed under vacuum (to avoid the presence of bubbles).

The level of catalyst is adjusted according to the pot life desired.

For approximately half of its composition (first component), the PUR is obtained from a so-called isocyanate part.

The other part of the composition used to prepare the PUR (second component) comprises the stable mixture of polyol, of adhesion promoter, of catalyst and, if appropriate, of dialkyl sulphoxide compound, in this case dimethyl sulphoxide (DMSO). The proportions of the isocyanate part and of the polyol part are calculated as a function of the equivalent weight of isocyanato group (NCO) and of the equivalent weight of hydroxyl group (OH), in order to have an NCO/OH ratio equal to 1.1.

The chemical nature and the amount of the polyols, of the polyisocyanate and of the catalyst of Examples 1 and 2 appear in the table below.

| Chemical nature of the components | Amount of each component (as % by weight) | |
|---|---|---|
| | Example 1 | Example 2 |
| Isocyanate component based on aliphatic isocyanate prepolymer obtained by reaction of an excess of aliphatic diisocyanate with glycerol | 49.3 | 49.3 |
| Polyol component based on ricinoleic acid polyesters type pentaerythritol ricinoleates. | 46.5 | 46.5 |
| Organotin catalyst. | 1.3 | 1.3 |
| Adhesion promoter (1) | 2.9 | 2.9 |
| DMSO | 0 | 2.4(2) |

(1) The commercial product Ethoduomeen T-13 from Akzo Co.
(2) corresponds to 4.9 parts by weight of DMSO per 100 parts of polyol component.

Potting of the Hollow Fibers

The potting with a polyurethane (PUR) -generating adhesive composition requires a prior drying, at least, of the ends of the bundle of fibers which will be in contact with the PUR.

The polyurethane-generating adhesive composition is subsequently prepared by mixing the first and second components mentioned in the preceding paragraph for the requirements of the examples.

Immediately afterwards, the composition is poured into a tank equipped with small tubes connected to the two ends of a tubular casing where a bundle of hollow fibers has been introduced and where it has to be potted at its two ends. Prior to this operation, the casing has been equipped with stoppers at its ends in order to contain the adhesive during the potting proper.

The casing comprising the bundle of fibers is rotated about an axis which is perpendicular to the longitudinal axis of the bundle and which passes through the mid-length of the device. Under the effect of the centrifugal force, the composition is displaced to the ends of the bundle of fibers and coats these. The composition also penetrates inside the fibers but this penetration is limited by the compression of the air trapped within the fibers. In addition, this penetration is controlled by varying two parameters: the centrifugal force (i.e. the rotational speed of the device) and the air temperature.

After polymerizing the composition, the stoppers are removed and the potting body is cut at a level beyond the penetration of the composition in the fibers, so that the fibers are open in order to allow circulation of fluid inside the fibers.

Once assembling is completed, the product obtained is hermetically packed in a bag in order to be protected from any microbiological contamination after sterilization.

The sterilization method chosen is gamma irradiation at an irradiation dose at least equal to 25 kGy, guaranteeing a negligible probability of microbiological contamination after sterilization.

Protocol for Measuring the Cytotoxicity of a Polyurethane (PUR)

In the examples, the cytotoxicity of the cured polyurethane (PUR) adhesive compositions was measured in accordance with the recommendations of ISO Standard 10-993, part 5, supplemented in the following way by the company Hospal:

On D1 (1st day), under aseptic conditions, a mouse fibroblast cell line (L929) is inoculated at low density at the bottom of culture wells (5000 cells per 0.32 cm$^2$ well). The cells, cultured in a culture medium to which has been added 10% of foetal calf serum (comprising growth factors), adhere to the plastic before dividing.

On D2 (2nd day), at the time when the cells enter into logarithmic growth phase, the cells are brought into contact with the aqueous eluate of the PUR studied, which is liable to comprise extractable substances.

The conditions for the preparation of the aqueous eluate of the PUR studied, in particular the surface area/volume and temperature/duration ratios, are described in ISO Standard 10-993, part 12.

The aqueous eluate of the PUR is diluted to half with a 2× (two times concentrated) culture medium. A dilution of the eluate to ¼ was also tested after dilution to half in a 1× culture medium of the preceding solution.

On D5 (5th day), the culture wells are emptied, the cellular layer is washed and the density and the viability of the cells are quantified using a standardized solution of a vital stain (neutral red) captured by living cells.

Approximately 3 hours later, the excess stain is removed by washing and the captured stain is extracted with a predetermined volume of a solution of acetic acid and of ethanol.

The cytotoxicity is determined with respect to an absolute growth control, where the 2H culture medium was diluted to half with water for injectable preparation (i.e., demineralized and doubly-distilled water), in which the cells are left for 5 days to become subconfluent, that is to say high density.

A positive control is systematically carried out using a toxic reference substance (HgCl$_2$, and the like). The preparation of the positive control involves diluting a 2H culture medium to half with water for injectable preparation, adding 6 μg/ml of HgCl$_2$ and leaving the cells for 5 days in this dilute toxic medium.

The relative cytotoxicity for each eluate is expressed, by difference with the absolute growth control, as percentage of inhibition of cell growth (% ICG).

The coloration of the solution of acetic acid and of ethanol depends on the concentration of living cells and is measured using a plate reader in the UV/visible, according to the following procedure:

ICG(%)=100(D−d)/D, where

D represents the optical density of the absolute growth control, d represents the optical density of the sample.

In addition, the results reported in the table below correspond to the average of three tested samples.

The results of the cytotoxicity measurements on the PURs of Examples 1 and 2 are reported in the table below.

| Example No. | % ICG of the eluate (37° C./120 h - 12 cm$^2$/1 ml) | |
| --- | --- | --- |
|  | Eluate diluated to ½ | Eluate diluated to ¼ |
| 1 | 57 | 14 |
| 2 | 18 | 0 |

In light of the results, it is clearly apparent that the presence of the compound DMSO in the PUR formulation of Example 2 results in the lowest values of inhibition of cell growth (% ICG). In accordance with the invention, the PUR of Example 2 is considered non-cytotoxic.

For a further understanding of the general structure of articles of manufacture of the invention, attention is invited to the patent and general literature and to FIG. 5 in the assignee's copending application Ser. No. 08/845,142, filed Apr. 21, 1997, by Burtin et al., entitled "Medical Apparatus for the Extracorporeal Treatment of Blood and Plasma, etc." and the description of FIG. 5 in the specification.

The preceding examples can be repeated with similar success by substituting the generically or specifically described reactant and/or operating conditions of this invention for those used in the preceding examples.

The entire disclosure of all applications, patents and publications, cited above and below, and of corresponding French application No. 97/10036, filed Jul. 31, 1997, is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In an article of manufacture comprising a polyurethane potting body in contact with a flat-membrane or hollow-fiber medical exchanger, so as to provide a leak-tight seal, the improvement wherein the potting body contains at least one dialkyl sulphoxide and is obtained from a polyurethane-generating composition comprising:
   at least one polyisocyanate, in the monomer or prepolymer state;
   at least one polyol; and
   at least one dialkyl sulphoxide compound in a sufficient amount to make the resultant potting body non-cytotoxic after oxidative sterilization.

2. An article of manufacture according to claim 1, wherein the polyurethane-generating composition additionally comprises a catalyst for the polymerization reaction of a polyisocyanate and of a polyol.

3. An article of manufacture according to claim 1, wherein the dialkyl sulphoxide compound has a melting point at most equal to 40° C.

4. An article of manufacture according to claim 3, wherein the dialkyl sulphoxide compound is liquid at ambient temperature .

5. An article of manufacture according to claim 4, wherein the dialkyl sulphoxide compound is dimethyl sulphoxide.

6. An article of manufacture according to claim 5, wherein the amount of dimethyl sulphoxide does not exceed 10% by weight with respect to the total weight of the polyol or polyols.

7. An article of manufacture according to claim 6, wherein the amount of dimethyl sulphoxide is between 3% and 9% by weight with respect to the total weight of the polyol or polyols.

8. An article of manufacture according to claim 1, wherein the polyisocyanate is non-aromatic.

9. A process for reducing the cytotoxicity of a polyurethane medical article after sterilization or disinfection by an oxidizing process, comprising providing a polyurethane-generating composition comprising at least one polyisocyanate, in the monomer or prepolymer state, at least one polyol and, optionally, at least one catalyst for the polymerization reaction of a polyisocyanate and of a polyol, and at least one dialkyl sulphoxide compound in the proportion of at least 2% by weight with respect to the total weight of the polyol or polyols, as a component of said medical article, and sterilizing or disinfecting said article by an oxidizing process.

10. A process according to claim 9, wherein the polyisocyanate is non-aromatic.

11. An article according to claim 1, wherein the polyisocyanate and polyol are polymerized and the resultant article is in the sterilized form.

12. An article of manufacture according to claim 1, wherein said at least one dialkyl sulfoxide compound is in a proportion of at least 2% by weight with respect to the total weight of said at least one polyol.

13. An article of manufacture according to claim 6, wherein said at least one dialkyl sulfoxide compound is in a proportion of at least 2% by weight with respect to the total weight of said at least one polyol.

14. An article of manufacture according to claim 7, wherein said at least one dialkyl sulphoxide compound is in a proportion of at least 2% by weight with respect to the total weight of said at least one polyol.

15. A process according to claim 9, wherein said at least one dialkyl sulphoxide is dimethyl sulphoxide.

16. In an article of manufacture comprising a polyurethane potting body in contact with a flat-membrane or hollow-fiber medical exchanger, the improvement wherein the potting body comprises polyurethane having incorporated therein at least one dialkyl sulphoxide compound, wherein said potting body is in the sterilized form.

17. An article according to claim 16, wherein the disulphoxide is dimethyl sulphoxide.

18. An article according to claim 1, further comprising a casing wherein said potting body seals said medical exchanger in a casing so as to provide two compartments divided by said medical exchanger and wherein said potting body prevents liquid from passing around said medical exchanger from one compartment to the other compartment.

19. An article according to claim 18, wherein said at least one dialkyl sulphoxide is dimethyl sulphoxide provided in a proportion of at least 2% by weight with respect to the total weight of the polyol or polyols.

* * * * *